United States Patent
Anderson (10) Patent No.: US 7,452,370 B2
(45) Date of Patent: Nov. 18, 2008

(54) APPARATUS FOR RETAINING A BONE ANCHOR IN A BONE PLATE AND METHOD FOR USE THEREOF

(75) Inventor: Kent Anderson, Memphis, TN (US)

(73) Assignee: Warsaw Orthopedic, Inc, Warsaw, IN (US)

( * ) Notice: Subject to any disclaimer, the term of this patent is extended or adjusted under 35 U.S.C. 154(b) by 320 days.

(21) Appl. No.: 11/118,841

(22) Filed: Apr. 29, 2005

(65) Prior Publication Data

US 2006/0247639 A1  Nov. 2, 2006

(51) Int. Cl.
*A61B 17/80* (2006.01)

(52) U.S. Cl. .................................... 606/296

(58) Field of Classification Search .............. 606/69–71
See application file for complete search history.

(56) References Cited

U.S. PATENT DOCUMENTS

| | | | |
|---|---|---|---|
| 5,364,399 A | 11/1994 | Lowery et al. | |
| 5,578,034 A | 11/1996 | Estes et al. | |
| 5,931,838 A | 8/1999 | Vito | |
| 6,258,089 B1 | 7/2001 | Campbell et al. | |
| 6,258,092 B1 | 7/2001 | Dall | |
| 6,261,291 B1 | 7/2001 | Talaber et al. | |
| 6,331,179 B1 | 12/2001 | Freid et al. | |
| 6,402,755 B1 | 6/2002 | Pisharodi | |
| 6,454,769 B2 | 9/2002 | Wagner et al. | |
| 6,599,290 B2 | 7/2003 | Bailey et al. | |
| 6,602,255 B1 | 8/2003 | Campbell et al. | |
| 6,652,525 B1 | 11/2003 | Assaker et al. | |
| 6,663,632 B1 | 12/2003 | Frigg | |
| 6,695,846 B2 | 2/2004 | Richelsoph et al. | |
| 6,755,833 B1 | 6/2004 | Paul et al. | |
| 6,764,489 B2 | 7/2004 | Ferree | |
| 6,884,242 B2 | 4/2005 | LeHuec et al. | |
| 7,322,984 B2 * | 1/2008 | Doubler et al. ............... 606/69 |
| 2001/0014807 A1 | 8/2001 | Wagner et al. | |
| 2002/0045896 A1 | 4/2002 | Michelson | |
| 2003/0187440 A1 | 10/2003 | Richelsoph et al. | |
| 2003/0187442 A1 | 10/2003 | Richelsoph et al. | |
| 2004/0015169 A1 * | 1/2004 | Gause ......................... 606/63 |
| 2004/0087951 A1 | 5/2004 | Khalili | |
| 2004/0097935 A1 | 5/2004 | Richelsoph et al. | |
| 2004/0127896 A1 | 7/2004 | Lombardo et al. | |
| 2004/0127899 A1 | 7/2004 | Konieczynski et al. | |
| 2004/0127900 A1 | 7/2004 | Konieczynski et al. | |

(Continued)

FOREIGN PATENT DOCUMENTS

EP  0 903 113 A2  8/1998

(Continued)

*Primary Examiner*—Eduardo C. Robert
*Assistant Examiner*—Nicholas Woodall
(74) *Attorney, Agent, or Firm*—Krieg DeVault LLP (57) ABSTRACT

A medical implant is provided that includes a bone plate having an aperture therethrough. The aperture receives a portion of the bone anchor. A retention mechanism is coupled to the bone plate. The retention mechanism includes a retainer and a biasing member. The biasing member is operatively engaged with at least the retainer. The insertion of the bone anchor in the aperture causes the retainer to move to a first position and elastically deform the biasing member. The biasing member causes the retainer to move to the second position to retain the bone anchor in the bone plate.

16 Claims, 7 Drawing Sheets

U.S. PATENT DOCUMENTS

| | | |
|---|---|---|
| 2004/0127904 A1 | 7/2004 | Konieczynski et al. |
| 2004/0260306 A1 | 12/2004 | Fallin et al. |
| 2005/0010227 A1 | 1/2005 | Paul |
| 2005/0049593 A1 | 3/2005 | Duong et al. |
| 2005/0192577 A1* | 9/2005 | Mosca et al. .............. 606/69 |
| 2005/0261690 A1* | 11/2005 | Binder et al. .............. 606/69 |
| 2005/0283152 A1 | 12/2005 | Lindemann et al. |
| 2006/0155285 A1 | 7/2006 | Anderson |

FOREIGN PATENT DOCUMENTS

| | | |
|---|---|---|
| EP | 1 169 971 | 1/2002 |
| EP | 1 500 376 A1 | 7/2004 |
| FR | 2 794 963 A1 | 6/1999 |
| WO | WO 2005/102192 | 11/2005 |

* cited by examiner

APPARATUS FOR RETAINING A BONE ANCHOR IN A BONE PLATE AND METHOD FOR USE THEREOF

BACKGROUND OF THE INVENTION

The present invention relates generally to bone plates, and more specifically, the present invention relates to a bone plate containing a retention mechanism for retaining one or more bone anchors in the bone plate and preventing the one or more bone anchors from becoming disengaged from said bone plate.

Various medical procedures involve fixation of boney elements in a patient. In particular, in medical procedures related to the spine, fixation of vertebral bodies may be performed as a result of trauma or a variety of spinal pathologies, abnormalities or disorders. In these medical procedures, fixation of the vertebral bodies is typically used to address instabilities in the spine or in relation to spinal fusion of the vertebral bodies. In this regard, fixation of the vertebral bodies provides mechanical stability and/or to reduce stress or movement in a particular area of the spine. Several mechanisms can be used in fixation of boney elements. One such device is a bone plate. In medical procedures related to the spine, the bone plate is fixed to and/or implanted into one or more vertebral bodies using one or more bone anchors. Often with the use of a bone plate, bone graft material and bone growth proteins are used in combination with implantation or fixation of the bone plate and/or when fusion of adjacent vertebral bodies is desired.

After the bone plate has been fixed to and/or implanted into one or more vertebral bodies of a patient, the bone plate and bone anchors are exposed to various stresses and forces due to the normal motion of the body and the spine of the patient. In particular, these stresses and forces may cause disengagement of the bone anchors from the bone plate. In addition, the stresses and forces may cause the bone plate or bone anchors to back out and/or pull away from one or more of the vertebral bodies into which the bone plate and bone anchors were attached. It is particularly undesirable for a bone anchor to pull away from the vertebral body or disengage from the bone plate.

Several types of retention mechanisms have been designed to prevent disengagement of a bone anchor from a bone plate. First, one design of a retention mechanism includes a cover plate that is separate from the bone anchor and the bone plate. In this design, the cover plate is an additional plate that is attached over the top of the bone plate to assist in the retention of the bone anchor in the bone plate. The cover plate requires an additional step of engaging the cover plate after the bone plate has been implanted or attached to one or more vertebral bodies. Secondly, another design includes retention mechanisms that are based in the bone anchor. Typically, this design includes a feature that is attached or integral with the bone anchor where the feature engages with the bone plate when the bone anchor is inserted in a boney element. Typically, these bone anchor based retention mechanisms are difficult to manufacture and fabricate, and, as such, increase the costs associated with the manufacturing of the bone anchor. In addition, even other retention mechanism designs include retention mechanisms that are attached to or integral with the bone plate. In these bone plate based designs, some retention mechanisms require a step of engaging the retention mechanism after a bone anchor has been inserted in the bone plate and/or in a boney element. In addition, other bone plate based retention mechanisms require specific placement of a portion of the bone anchor before, during or after insertion of the bone anchor in the bone plate or in a boney element. Also, in even another bone plate based retention mechanism, the use of inserts or collars in or around the bone anchor is required to retain the bone anchor in the bone plate. Typically, these inserts and collars require the insertion of the bone anchor to be at specifically designed angles or orientation relative to the bone plate.

Based on these prior retention mechanisms, there is a desire in the art for a bone plate having a retention mechanism that does not require the attachment of an additional plate to retain the bone anchors in the bone plate. Further, there is also a desire for a bone retention mechanism that does not substantially increase the cost of manufacturing or fabrication of the bone plate or any associated bone anchors. In addition, there is a desired for a retention mechanism that does not require an additional step of engaging the retention mechanism after a bone anchor has been inserted in the bone plate or attached to a boney element. Also, there is a desire for a retention mechanism that does not require specific placement of a portion of a bone anchor before, during or after insertion of the bone anchor in the bone plate or the boney element. Additionally, there is a desire for a retention mechanism that can accommodate variable angle bone anchors and a mechanism that allows a bone anchor to be inserted at multiple and/or different angles or orientations. Ultimately, there is a desire for a retention mechanism that has uncomplicated operation, and that affords rigid, yet, reversible retention of a bone anchor in a bone plate.

BRIEF SUMMARY OF THE INVENTION

In one embodiment, a medical implant is provided that uses a bone anchor to attach the medical implant to a boney element. The medical implant includes a bone plate that has an aperture therethrough. The aperture receives at least a portion of the bone anchor. A retention mechanism is coupled to the bone plate. The retention mechanism includes a retainer and a biasing member, and the biasing member is operatively engaged with at least the retainer. The retainer is moveable to and from at least a first position and a second position. The first position allows the bone plate to receive the bone anchor in the aperture. The second position allows the retention mechanism to retain the bone anchor in the bone plate. The insertion of the bone anchor in the aperture causes the retainer to move to the first position and elastically deform the biasing member. The biasing member causes the retainer to move to the second position to retain the bone anchor in the bone plate.

In another embodiment, a medical implant is provided that uses a first and second bone anchor to attach the medical implant to a boney element. The medical implant includes a bone plate that has a first aperture and a second aperture. The first and second apertures are located through the bone plate. The first aperture receives at least a portion of the first bone anchor. The second aperture receives at least a portion of the second bone anchor. A retention mechanism is coupled to the bone plate. The retention mechanism includes a retainer and a biasing member that engages with at least the retainer. The retainer is moveable to and from at least a first position, a second position and a third position. The first position allows the bone plate to receive the first bone anchor in the first aperture. The second position allows the bone plate to receive the second bone anchor in the second aperture. The third position allows the retention mechanism to retain the first and second bone anchors in the bone plate. The insertion of the first bone anchor in the first aperture causes the retainer to move to the first position and elastically deform the biasing member. The insertion of the second bone anchor in the second aperture causes the retainer to move to the second position and elastically deform the biasing member. The biasing member causes the retainer to move to the third position to retain the first and second bone anchors in the bone plate.

In even another embodiment, a method for retaining a bone anchor in a medical implant is provided. The method includes providing a bone plate having an aperture located therethrough. The bone plate also includes a retention mechanism that has a retainer and a biasing member. The retainer is moveable to and from at least a first position and a second position. The first position allows the bone plate to receive the bone anchor in the aperture. The second position allows the retention mechanism to retain the bone anchor in the bone plate. The bone anchor is inserted in the aperture. A head of the bone anchor is caused to contact the retention mechanism during the insertion of the bone anchor in the aperture. The retainer is moved to the second position when the head of the bone anchor make contact with the retainer. The biasing member is elastically deformed when the retainer is moved from the first position to the second position. The head of the bone anchor is retained in the aperture when a portion of the bone anchor is positioned below a portion of the retention mechanism. The retainer is moved from the second position to the first position using a force provided from elastic deformation of the biasing member. The bone anchor is retained in the bone plate when the retainer is in the first position.

DETAILED DESCRIPTION OF THE INVENTION

For the purpose of promoting an understanding of the principles of the invention, reference will be made to the embodiments illustrated in the drawings and specific language will be used to describe the same. It will nevertheless be understood that no limitation of the scope of the invention is hereby intended nor should be construed. Any such alterations and further modifications in the illustrated devices and described methods, and any such further applications of the principles of the invention as illustrated herein are contemplated as would normally occur to one skilled in the art to which the invention relates.

Figure 1:
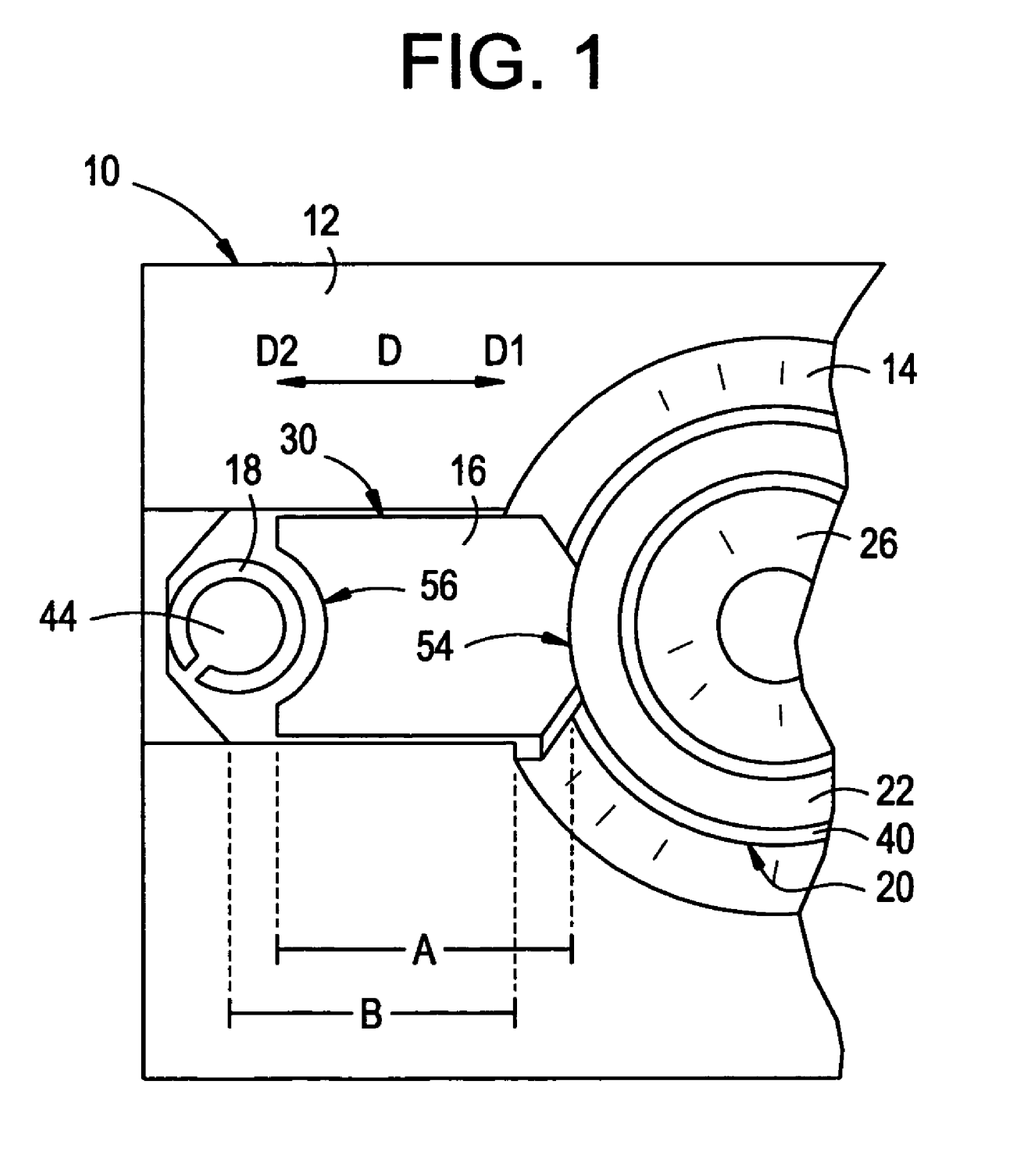
FIG. 1 is a partial three-dimensional top view of one embodiment of a bone plate.
Figure 2:
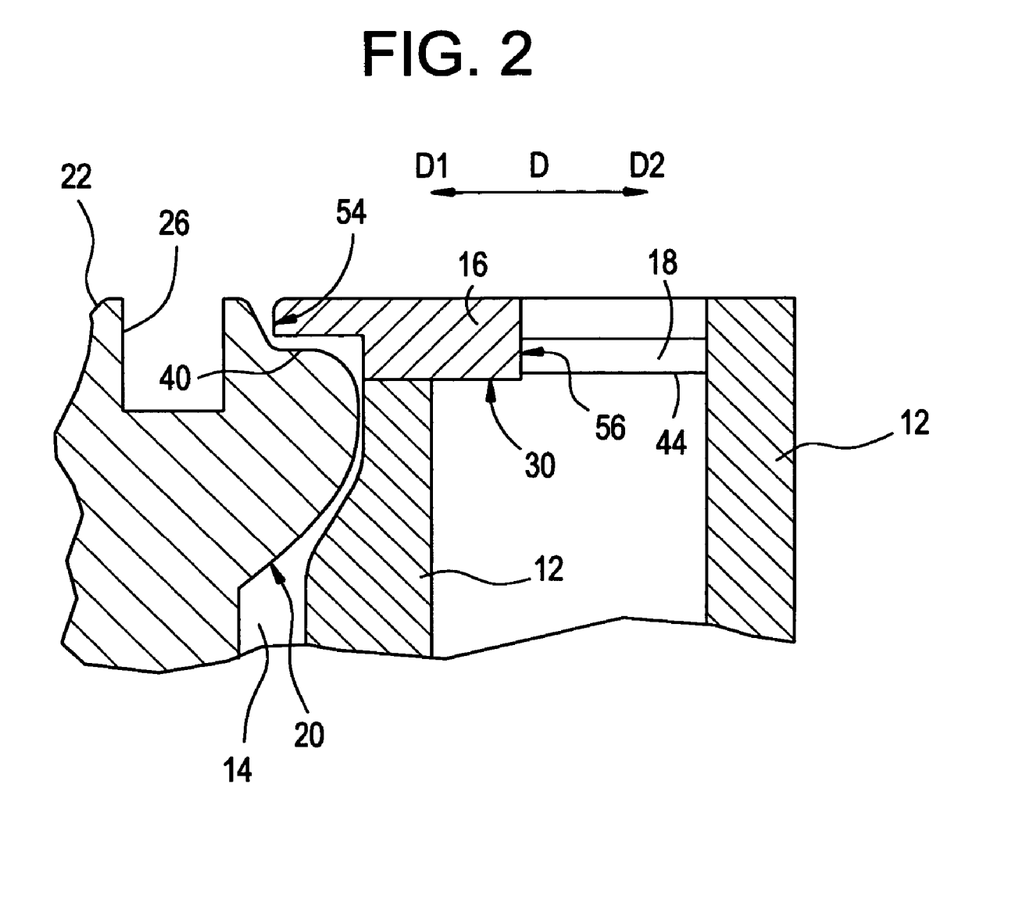
FIG. 2 is a cross-sectional view of one embodiment of a bone plate, retention mechanism and bone anchor.

In one embodiment as shown in FIGS. 1 and 2, a medical implant 10 is provided that is secured to a boney element using a bone anchor 20. It should be appreciated that, in one embodiment, the boney element can comprise at least one vertebral body of the spinal column. It should also be appreciated that the bone anchor 30 can comprise, for example, a screw, a multi-axial screw, a staple or a spike. The medical implant 10 includes a bone plate 12 having an aperture 14. The aperture 14 comprises a hole or opening that is located through the bone plate 12. The bone anchor 20 includes a head 22. The bone plate 12 is adapted to hold the head 22 in the aperture 14 without allowing the head 22 to pass completely through the bone plate 12. The head 22 also includes a receiving portion 26 that is positioned on a top surface 70 (FIG. 3) of the head 22. It should be appreciated that the receiving portion 26 is adapted and/or shaped to receive a bit from a driver that is used to insert the bone anchor 20 into the bone element. It should further be appreciated that the receiving portion 26, shown in FIGS. 1 and 2, is a female portion. In another embodiment, the receiving portion 26 can comprise a male portion. As further shown in FIG. 1, a retention mechanism 30 is coupled to the bone plate 12. The retention mechanism 30 includes a retainer 16 and a biasing member 18. The retainer 16 has a first end 54 and a second end 56, and the first end 54 is located opposite from the second end 56. The first end 54 of the retainer 16 includes a contoured edge 36. The second end 56 of the retainer 16 is operatively engaged with the biasing member 18. The biasing member 18 is located in seat 44 in bone plate 12. In one embodiment, the biasing member 18 is a spring. In another embodiment, the biasing member 18 is a flexible ring. In even another embodiment, the biasing member 18 is a shape memory alloy. In one embodiment, the shape memory alloy comprises a nickel-titanium alloy, such as, nitinol.

As shown in FIG. 1, the retainer 16 is moveable in the bone plate 12 to at least a first position A and a second position B. In the first position A, the retainer 16 retains the bone anchor 20 in the bone plate 12. In the second position B, the retainer 16 allows the bone anchor 20 to be inserted in the aperture 14. It should be appreciated that when the bone anchor 20 is retained in the bone plate 12, the bone anchor 20 is prevented from backing out of the aperture 14 and is held with the bone plate 12 in the aperture 14. As further shown in FIG. 1, bone anchor 20 includes an engagement portion 40. In one embodiment, when the retainer 16 is in the first position A and after the bone anchor 20 has been inserted in the aperture 14, the contoured edge 36 of the retainer 16 is positioned adjacent to the engagement portion 40, and, thus, the retainer 16 prevents the bone anchor 20 from backing out of the aperture 14. It should be appreciate that in another embodiment, the contoured edge 36 is in contact or touches the engagement portion 40 of the bone anchor 20 when the retainer 16 is in the first position A. Thus, in this position, the retainer 16 retains the bone anchor 20 in the bone plate 12 and prevents the bone anchor 20 from backing out of the aperture 14.

As also shown in FIG. 1, before the bone anchor 20 has been inserted into the aperture 14 of the bone plate 12, the retainer 16 of the retention mechanism 30 is, typically, in the first position A. In one embodiment, the biasing member 18 holds the retainer 16 in the first position A via a biasing force from the biasing member 18. As the bone anchor 20 is inserted into the aperture 14, a threaded portion 24 (FIG. 3) of the bone anchor 20 passes through the aperture 14 of the bone plate 12. Further, as the bone anchor 20 continues to be inserted into the aperture 14, the head 22 of the bone anchor 20 comes into contact with the retainer 16. As the head 22 contacts the retainer 16, the retainer 16 moves in direction D2, and this movement elastically deforms the biasing member 18. The movement of the retainer 16 in the direction D2 is caused by the force of a user inserting the bone anchor 20 into the aperture 14. As the bone anchor 20 continues to be inserted, the retainer 16 will continue to move in the direction D2 until the retainer 16 is in the second position B. It should be appreciated that the second position B allows the widest portion of the head 22 of the bone anchor 20 to be inserted into the aperture 14. After the widest portion of the head 22 has been inserted into the aperture 14, the biasing member 18 will cause the retainer 16 to snap back and/or move back into the first position A. The elastic deformation of the biasing member 18 caused by the insertion of the bone anchor 20 into the aperture 14 causes the biasing member 18 to exert a force in the direction of D1 after the widest portion of the bone anchor 20 has been inserted into the aperture 14. This force from the biasing member 18 causes the retainer 16 to snap back, return and/or move to the first position A in the direction D1. After the retainer 16 has moved back to the first position A, a portion of the head 22 is positioned below a portion of the retainer 16. Further, when the biasing member 18 causes the retainer 16 to snap back and/or move back to the first position A, a portion of the first end 54 of the retainer 16 will cover or be positioned over a portion of the head 22. In one embodiment, when the portion of the first end 54 of the retainer 16 is positioned over the head 22 of the bone anchor 20, the contoured edge 36 of the retainer 16 is positioned over the engagement portion 40 of the bone anchor 20. This positioning of the contoured edge 36 over the engagement portion 40 of the bone anchor 20 retains the bone anchor 20 in the bone plate 12 preventing back out of the bone anchor 20 from the aperture 14. It should be appreciated that, in one embodiment, the movement of the retainer 16 along line D, and in the directions of D1 and D2, is movement in a linear direction relative to a top surface 70 (FIG. 3) of the bone plate 12. It should be appreciated that the bone anchor 20 can be removed from the aperture 14 of the bone plate 12 after the bone anchor 20 has been inserted and has been retained in the bone plate 12. To remove the bone anchor 20, the retainer 16 is moved manually to position B via an instrument or by user. Once the retainer 16 is moved to and held in position B, the bone anchor 20 can be removed from the aperture 14 by, for example, pulling or by unscrewing the bone anchor 20 from the boney element. As such, retention of the bone anchor 20 in the bone plate 12 is reversible by a user.

Figure 3:
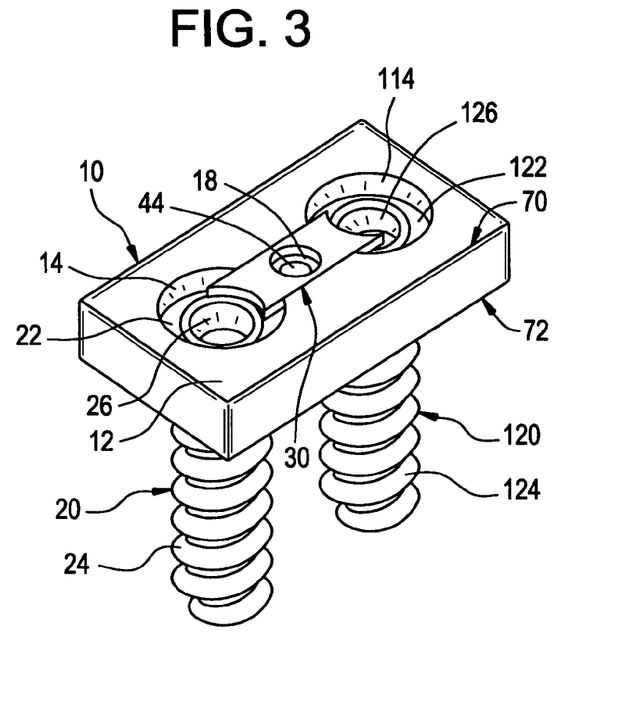
FIG. 3 is a perspective view of one embodiment of a bone plate, a retention mechanism and bone anchors.
Figure 4:
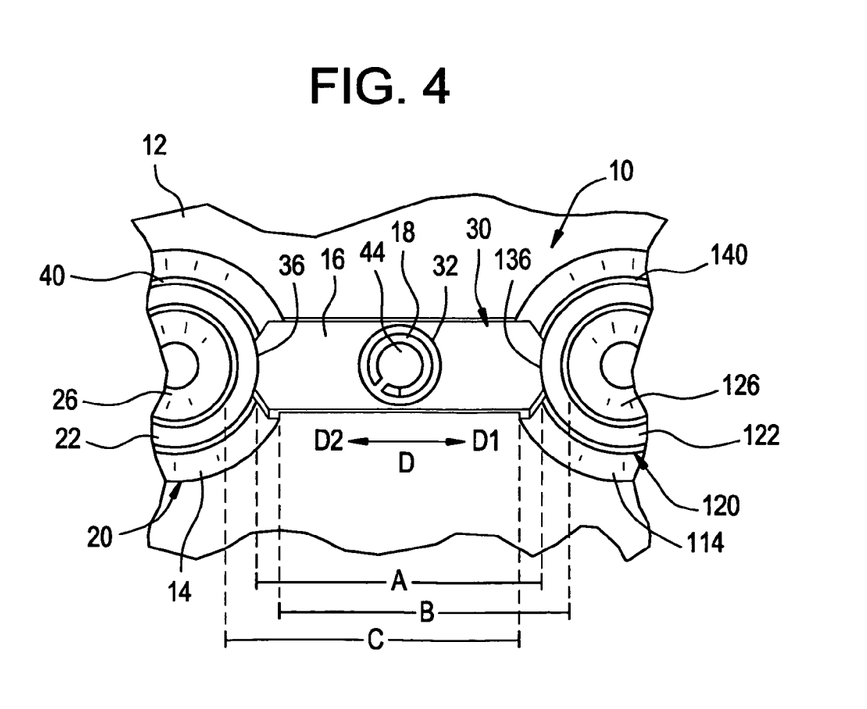
FIG. 4 is a partial three-dimensional top view of another embodiment of a bone plate with a retention mechanism.

In another embodiment, as shown in FIGS. 3 and 4, the medical implant 10 includes a bone plate 12, a first bone anchor 20 and a second bone anchor 120. As shown in FIG. 3, the bone plate 12 includes a top surface 70 and a bottom surface 72. It should be appreciated that, when implanted in a patient, the bottom surface 72 of the bone plate 12 is located adjacent or abutting the boney element that the first and second bone anchors 20 and 120 are attached. Further, the bone plate 12 includes a first aperture 14 and a second aperture 114. As also shown in FIGS. 3 and 4, the medical instrument 10, shown in FIG. 3, is attached to the boney element using a first bone anchor 20 and a second bone anchor 120. Similar to the description hereinabove, the first bone anchor 20 includes a threaded portion 24 and a head 22, and the second bone anchor 120 also includes a threaded portion 124 and a head 122. Additionally, the head 22 of bone anchor 20 includes a receiving portion 26 and an engagement portion 40. Similarly, the head 122 of bone anchor 120 also includes a receiving portion 126 and an engagement portion 140.

In one embodiment, as shown in FIGS. 3 and 4, the retention mechanism 30 is coupled to the bone plate 12. The retention mechanism 30 includes a retainer 16 and a biasing portion 18. The biasing portion 18 is positioned in seat 44 in bone plate 12 and is also positioned in an opening 32 in the retainer 16. In this embodiment, the retainer 16 is capable of holding the first bone anchor 20 in the first aperture 14 and also capable of holding the second bone anchor 120 in the second aperture 114. As shown in FIG. 4, the retainer 16 is moveable in the bone plate 12 to at least a first position A, a second position B and a third position C. In the first position A, the retainer 16 retains the first bone anchor 20 and the second bone anchor 120 in the bone plate 12. In the second position B, the retainer 16 allows the first bone anchor 20 to be inserted in the first aperture 14. In the third position C, the retainer 16 allows the second bone anchor 120 to be inserted in the second aperture 114. It should be appreciated that when the first bone anchor 20 and second bone anchor 120 are retained in the bone plate 12, the first bone anchor 20 and the second bone anchor 120 are prevented from backing out of the first and second apertures 14 and 114, respective, and are held with the bone plate 12 in the first and second apertures 14 and 114, respectively. As further shown in FIG. 4, first bone anchor 20 includes an engagement portion 40, and second bone anchor 120 includes an engagement portion 140. When the retainer 16 is in the first position A and after the first bone anchor 20 and second bone anchor 120 have been inserted in the first and second apertures 14 and 114, respectively, the first and second contoured edges 36 and 136 of the retainer 16 are positioned adjacent to the engagement portion 40 and engagement portion 140, respectively. Thus, in this position, the retainer 16 retains the first bone anchor 20 and the second bone anchor 120 in the first and second apertures 14 and 114, respectively. It should be appreciate that in another embodiment, the first and second contoured edges 36 and 136 are in contact or touch the first engagement portion 40 and the second engagement portion 140, respectively, when the retainer 16 is in the first position A, and, thus, the retainer 16 retains the first and second bone anchor 20 and 120 in the first and second apertures 14 and 114, respectively.

As explained above and shown in FIG. 4, before the first bone anchor 20 and the second bone anchors 120 have been inserted into the first aperture 14 and second apertures 114, respectively, of the bone plate 12, the retainer 16 of the retention mechanism 30 is, typically, in the first position A. In one embodiment, the biasing member 18 holds the retainer 16 in the first position A via a biasing force from the biasing member 18. As the first bone anchor 20 is inserted into the first aperture 14, a threaded portion 24 of the first bone anchor 20 passes through the first aperture 14 of the bone plate 12. Further, as the first bone anchor 20 continues to be inserted into the first aperture 14, the head 22 of the first bone anchor 20 comes into contact with the retainer 16. As the head 22 contacts the retainer 16, the retainer 16 moves in direction D1 and this movement elastically deforms the biasing member 18. The movement of the retainer 16 in the direction D1 is caused by the force of a user inserting the first bone anchor 20 into the first aperture 14. As the first bone anchor 20 continues to be inserted, the retainer 16 will continue to move in the direction D1 until the retainer 16 is in the second position B. It should be appreciated that the second position B allows the widest portion of the head 22 of the first bone anchor 20 to be inserted into the first aperture 14. After the widest portion of the head 22 has been inserted into the first aperture 14, the biasing member 18 will cause the retainer 16 to snap back and/or move back into the first position A in the direction D2. The elastic deformation of the biasing member 18 caused by the insertion of the first bone anchor 20 into the first aperture 14 causes the biasing member 18 to exert a force in the direction of D2 after the widest portion of the first bone anchor 20 has been inserted into the first aperture 14. This force from the biasing member 18 causes the retainer 16 to snap back, return and/or move to the first position A. After the retainer 16 has moved back to the first position A, a portion of the head 22 is positioned below a portion of the retainer 16. Further, when the biasing member 18 causes the retainer 16 to snap back and/or move back to the first position A, a portion of the first contoured end 36 of the retainer 16 will cover or be positioned over a portion of the head 22. In one embodiment, when the portion of the first contoured edge 36 of the retainer 16 is positioned over the head 22 of the first bone anchor 20, the first contoured edge 36 of the retainer 16 is positioned over the first engagement portion 40 of the first bone anchor 20. This positioning of the first contoured edge 36 over the first engagement portion 40 of the first bone anchor 20 retains the first bone anchor 20 in the bone plate 12 preventing back out of the first bone anchor 20 from the first aperture 14.

With reference to the second bone anchor 120, as the second bone anchor 120 is inserted into the second aperture 114, a threaded portion 124 of the second bone anchor 120 passes through the second aperture 114 of the bone plate 12. Further, as the second bone anchor 120 continues to be inserted into the second aperture 114, the head 122 of the second bone anchor 120 comes into contact with the retainer 16. As the head 122 contacts the retainer 16, the retainer 16 moves in direction D2 and this movement elastically deforms the biasing member 18. The movement of the retainer 16 in the direction D2 is caused by the force of a user inserting the second bone anchor 120 into the second aperture 114. As the second bone anchor 120 continues to be inserted, the retainer 16 will continue to move in the direction D2 until the retainer 16 is in the third position C. It should be appreciated that the third position C allows the widest portion of the head 122 of the second bone anchor 120 to be inserted into the second aperture 114. After the widest portion of the head 122 has been inserted into the second aperture 114, the biasing member 18 will cause the retainer 16 to snap back and/or move back into the first position A in the direction D2. The elastic deformation of the biasing member 18 caused by the insertion of the second bone anchor 120 into the second aperture 114 causes the biasing member 18 to exert a force in the direction of D1 after the widest portion of the second bone anchor 120 has been inserted into the second aperture 114. This force from the biasing member 18 causes the retainer 16 to snap back, return and/or move to the first position A. After the retainer 16 has moved back to the first position A, a portion of the head 122 is positioned below a portion of the retainer 16. Further, when the biasing member 18 causes the retainer 16 to snap back and/or move back to the first position A, a portion of the second contoured end 136 of the retainer 16 will cover or be positioned over a portion of the head 122. In one embodiment, when the portion of the second contoured end 136 of the retainer 16 is positioned over the head 122 of the second bone anchor 120, the second contoured edge 136 of the retainer 16 is positioned over the second engagement portion 140 of the second bone anchor 120. This positioning of the second contoured edge 136 over the second engagement portion 140 of the second bone anchor 120 retains the second bone anchor 120 in the bone plate 12 preventing back out of the second bone anchor 120 from the second aperture 114. It should be appreciated that, in one embodiment, the movement of the retainer 16 along line D, and in the directions of D1 and D2, is movement in a linear direction relative to a top surface 70 of the bone plate 12.

As shown in FIG. 3, the aperture 14 has an interior portion that extends from a top surface 70 to a bottom surface 72. In one embodiment, the interior portion can be a cylindrical shape. The top surface 70 is oppositely located from the bottom surface 72, and the bottom surface 72 is, typically, located adjacent to the boney element when the medical implant 10 is implanted in a patient. The bone anchor 20 includes a head 22 and a threaded portion 24. In one embodiment, the diameter of the threaded portion 24 is smaller than the diameter of the head 22. The aperture 14 is sized to allow the threaded portion 24 to pass through the bone plate while the head 22 is held by the aperture 14 and is not allowed to pass completely through the bone plate 12. To accomplish the passing of the threaded portion 24 and the holding of the head 22, the aperture 14 is wider at the top surface 70 of the bone plate 12 and narrower at the bottom surface 72 of the bone plate 12. In one embodiment, the interior portion of the aperture 14 can be tapered from the top surface 70 to the bottom surface 72.

Figure 5:
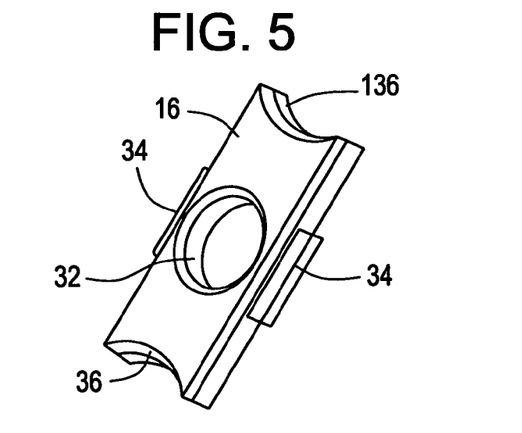
FIG. 5 is front view of one embodiment of a retainer.
Figure 6:
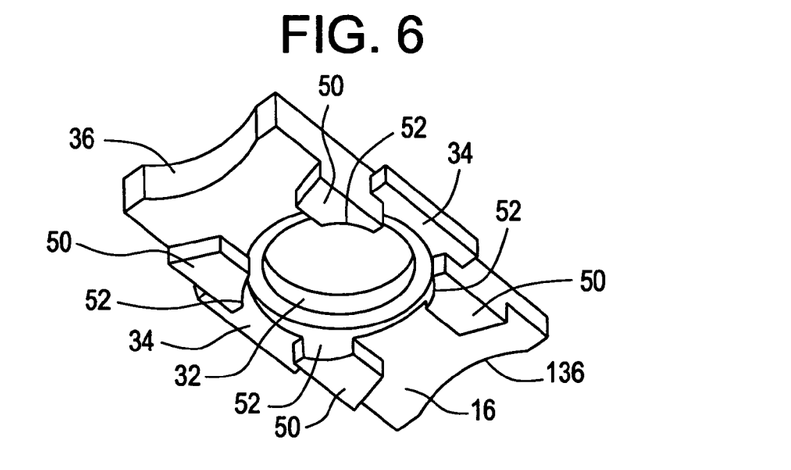
FIG. 6 is a bottom view of one embodiment of a retainer.
Figure 7:
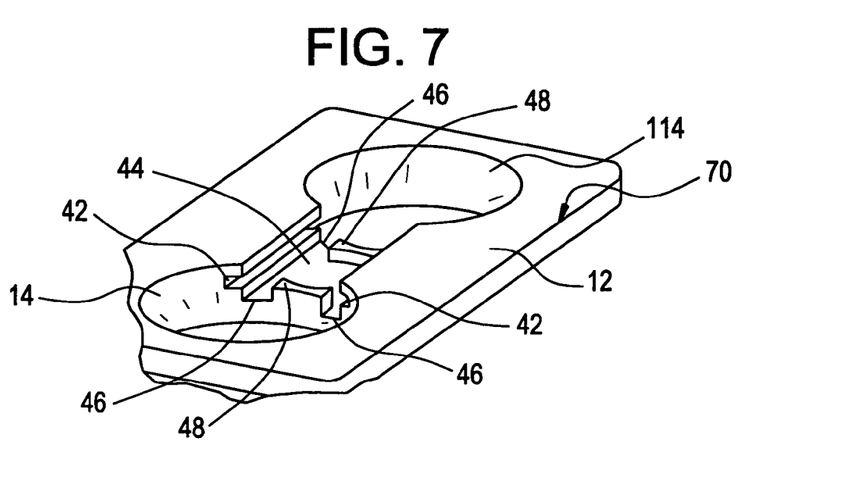
FIG. 7 is a partial three-dimensional top view of another embodiment of a bone plate.

In FIG. 5, one embodiment of a retainer 16 includes tabs 34 positioned on side portions of the retainer 16. An opening 32 is positioned in the retainer 16. Also shown in FIG. 6, a bottom of the retainer 16 is provided. In one embodiment, the bottom of the retainer 16 is the portion of the retainer 16 that faces the head 22 of the bone anchor 20 when the bone anchor 20 is inserted in the aperture 14. The bottom of the retainer 16 includes four contacting portions 50 positioned about the opening 32. Each of the contacting portions 50 contains an edge 52. As shown in FIG. 7, in one embodiment, the bone plate 12 includes channels 42, grooves 46, stops 48 and a seat 44 that are positioned between the first and second apertures 14 and 114. The grooves 42 are adapted to accept the tabs 34 of the retainer 16. When the retainer 16 moves to and from the various positions, the tabs 34 of the retainer 16 move within the channels 42 of the bone plate 12. Further, the channels 42 also hold the retainer 16 in the bone plate 12. In this regard, the tabs 34 are slidabely engaged within the channel 42 such that the channels 42 capture the tabs 34 within the bone plate 12. In addition, as the tabs 34 are engaged in the channels 42, the contacting portions 50 of the retainer 16 are moveable through the grooves 46 in the bone plate 12. Further, the seat 44 accepts the biasing member 18, and the biasing member 18 is held in the seat 44 by stops 48. In one embodiment, the biasing member 18 comprises a flexible ring. When placed into position, the retaining member 18 is placed into the seat 44 such that the retaining member 18 is biased against the stops 48. As such, a biasing force is exerted by the retaining member 18 against the stops 48, and this biasing force holds the biasing member 18 into place in the seat 44.

In this embodiment, the retention mechanism 30 is coupled to the bone plate 12 by sliding the tabs 34 of the retainer 16 into the channels 42. As mentioned above, as the tabs 34 are engaged into the channels 42, the contacting portions 50 of the retainer 16 slide through the grooves 46 in the bone plate 12. The tabs 34 of the retainer 16 are moved through the channels 42 until the opening 32 of the retainer 16 is positioned over the seat 44. When the opening 32 is positioned over the seat 44, the biasing member 18 is inserted through the opening 32 into the seat 44. As mentioned above, the biasing member 18 is biased against the stops 48 and held into place in the bone plate 12. This position of the retainer 16 corresponds to position A, as shown in FIG. 4. After the retention mechanism 30 has been coupled to the bone plate 12, the biasing member 18 affects the movement of the retainer 16. If the retainer 16 is moved, the edges 52 of the contacting portions 50 on the retainer 16 will contact the biasing member 18 as the contacting portion 50 moves through the grooves 46.

The contact of the edges 52 with the biasing member 18 creates a force from the biasing member 18. This force will cause the biasing member 18 to return the retainer 16 back to the position A (FIG. 4). As such, the retention mechanism 30 is capable of moving in various positions to allow insertion of the bone anchors 20 and 120, and the retainer 16 will return back to position A (FIG. 4) due to forces exerted by the biasing member 18. It should be appreciated that in this movement of the retainer 16 forces from the biasing member 18 do not require any interaction by a user.

Figure 8:
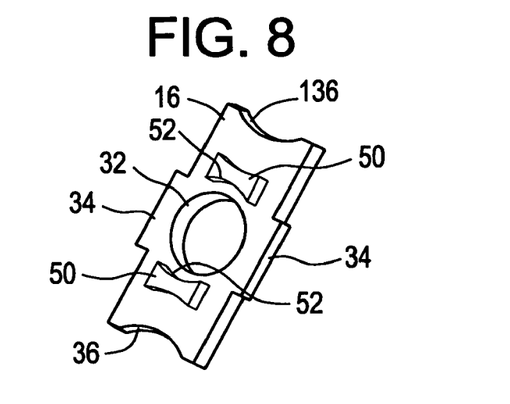
FIG. 8 is a bottom view of another embodiment of a retainer.
Figure 9:
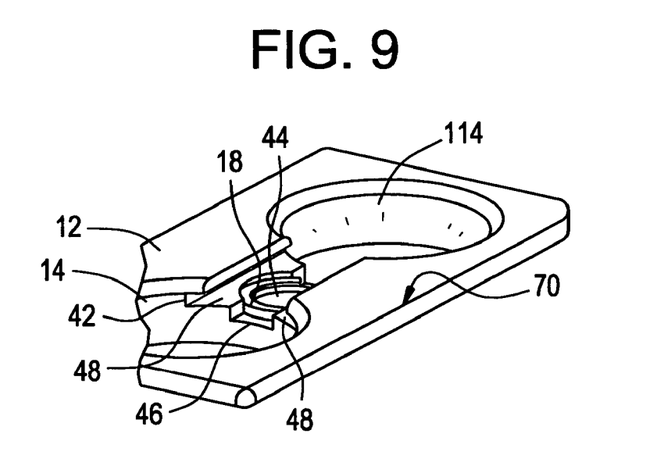
FIG. 9 is a partial three-dimensional top view of even another embodiment of a bone plate.

In another embodiment, as shown in FIG. 8, the retainer 16 includes two contacting portions 50 positioned about the opening 32 and on opposite sides thereof. In this embodiment, the bone plate 12 includes grooves 46 that are positioned to accept the contacting portions 50. The coupling and operation of the retention mechanism 30 in this embodiment is similar to that discussed above with reference to FIGS. 5 and 6.

Figure 10:
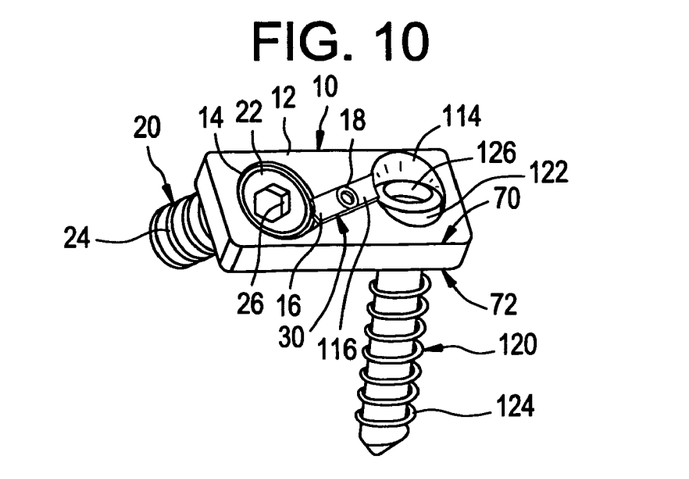
FIG. 10 is a perspective view of even embodiment of a bone plate, a retention mechanism and bone anchors.
Figure 11:
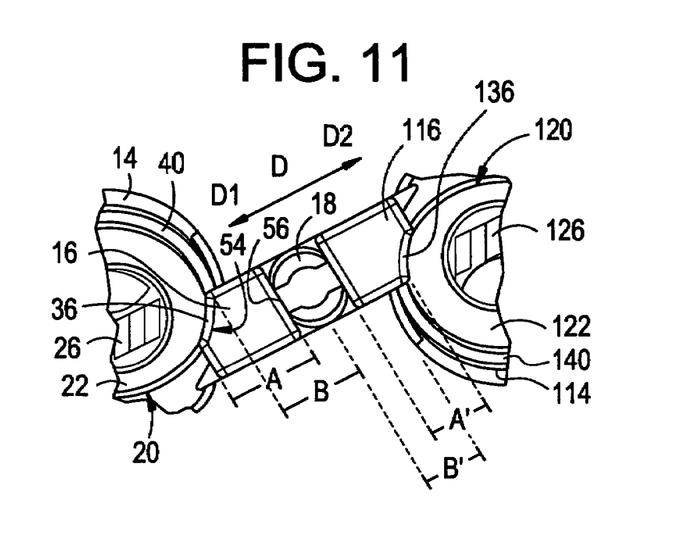
FIG. 11 is a partial three-dimensional top view of yet another embodiment of a bone plate.

In even another embodiment, as shown in FIG. 10, the medical implant 10 includes a retention mechanism 30 coupled to the bone plate 12. In this embodiment, the retention mechanism 30 includes a biasing member 18 that is adapted to engage a first retainer 16 and a second retainer 116. In the embodiment, shown in FIG. 10, the bone plate 12 accepts first and second bone anchors 20 and 120 that are inserted into a first aperture 14 and a second aperture 114, respectively. In one embodiment, the first and second bone anchors 20 and 120 are inserted at different angles with respect to each other and/or with respect to the bone plate 12. As shown in FIG. 11, the first retainer 16 includes a first contoured edge 36 and the second retainer 116 includes a second contoured edge 136. As discussed hereinabove, the first and second contoured edges 36 and 136 can contact or be placed adjacent to the first and second engagement portions 40 and 140, respectively, to retain the first and second bone anchors 20 and 120, respectively, in the bone plate 12. Further, the biasing member 18 holds the first and second retainers 16 and 116 in the first position A and A', respectively, via a biasing force from the biasing member 18.

As shown in FIG. 11, with respect to the first retainer 16, as the first bone anchor 20 is inserted into the first aperture 14, a threaded portion 24 of the first bone anchor 20 passes through the first aperture 14 of the bone plate 12. Further, as the first bone anchor 20 continues to be inserted into the first aperture 14, the head 22 of the first bone anchor 20 comes into contact with the first retainer 16. As the head 22 contacts the first retainer 16, the first retainer 16 moves in direction D1 and this movement elastically deforms the biasing member 18. The movement of the first retainer 16 in the direction D1 is caused by the force of a user inserting the first bone anchor 20 into the first aperture 14. As the first bone anchor 20 continues to be inserted, the first retainer 16 will continue to move in the direction D1 until the first retainer 16 is in the second position B. It should be appreciated that the second position B allows the widest portion of the head 22 of the first bone anchor 20 to be inserted into the first aperture 14. After the widest portion of the head 22 has been inserted into the first aperture 14, the biasing member 18 will cause the first retainer 16 to snap back and/or move back into the first position A. The elastic deformation of the biasing member 18 caused by the insertion of the first bone anchor 20 into the first aperture 14 causes the biasing member 18 to exert a force in the direction of D2 after the widest portion of the first bone anchor 20 has been inserted into the first aperture 14. This force from the biasing member 18 causes the first retainer 16 to snap back, return and/or move to the first position A in the direction D2. After the first retainer 16 has moved back to the first position A, a portion of the head 22 is positioned below a portion of the first retainer 16. Further, when the biasing member 18 causes the first retainer 16 to snap back and/or move back to the first position A, a portion the first retainer 16 will cover or be positioned over a portion of the head 22. In one embodiment, when the portion of the first retainer 16 is positioned over the head 22 of the first bone anchor 20, the first contoured edge 36 of the first retainer 16 is positioned over the first engagement portion 40 of the first bone anchor 20. This positioning of the first contoured edge 36 over the first engagement portion 40 of the first bone anchor 20 retains the first bone anchor 20 in the bone plate 12 preventing back out of the first bone anchor 20 from the first aperture 14. It should be appreciated that, in one embodiment, the movement of the first retainer 16 along line D, and in the directions of D1 and D2, is movement in a linear direction relative to a top surface 70 of the bone plate 12.

As also shown in FIG. 11, the operation of the second retainer 116 is similar to the operation described in reference to the first retainer 16. However, the second retainer 116 is positioned in first position A' and second position B'. In addition, movement along the line D for the second retainer 116 is opposite from the movement of the first retainer 16. In this regard, the second retainer 116 is moved in the direction of D2 to allow the second bone anchor 120 to be inserted into the second aperture 114, and the second retainer 116 will snap back or move in the direction of D1 from the force supplied by the biasing member 18 when the second retainer 116 is moved.

Figure 12:
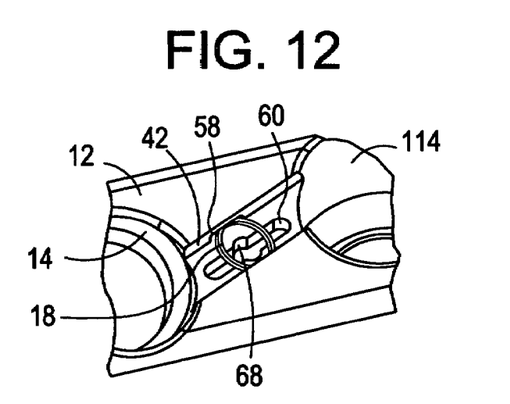
FIG. 12 is a partial three-dimensional top view of yet another embodiment of a bone plate.
Figure 13:
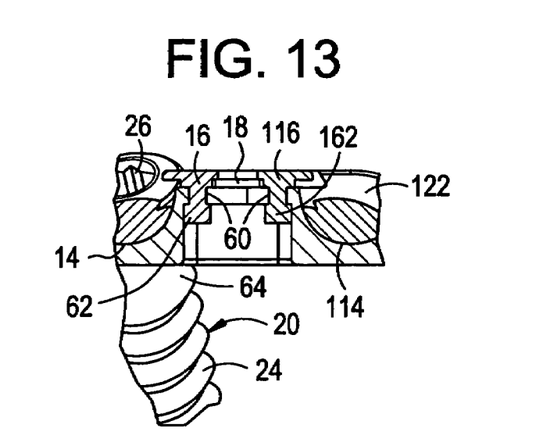
FIG. 13 is a partial cross-sectional view of yet another embodiment of a bone plate, retention mechanism and bone anchors.
Figure 14:
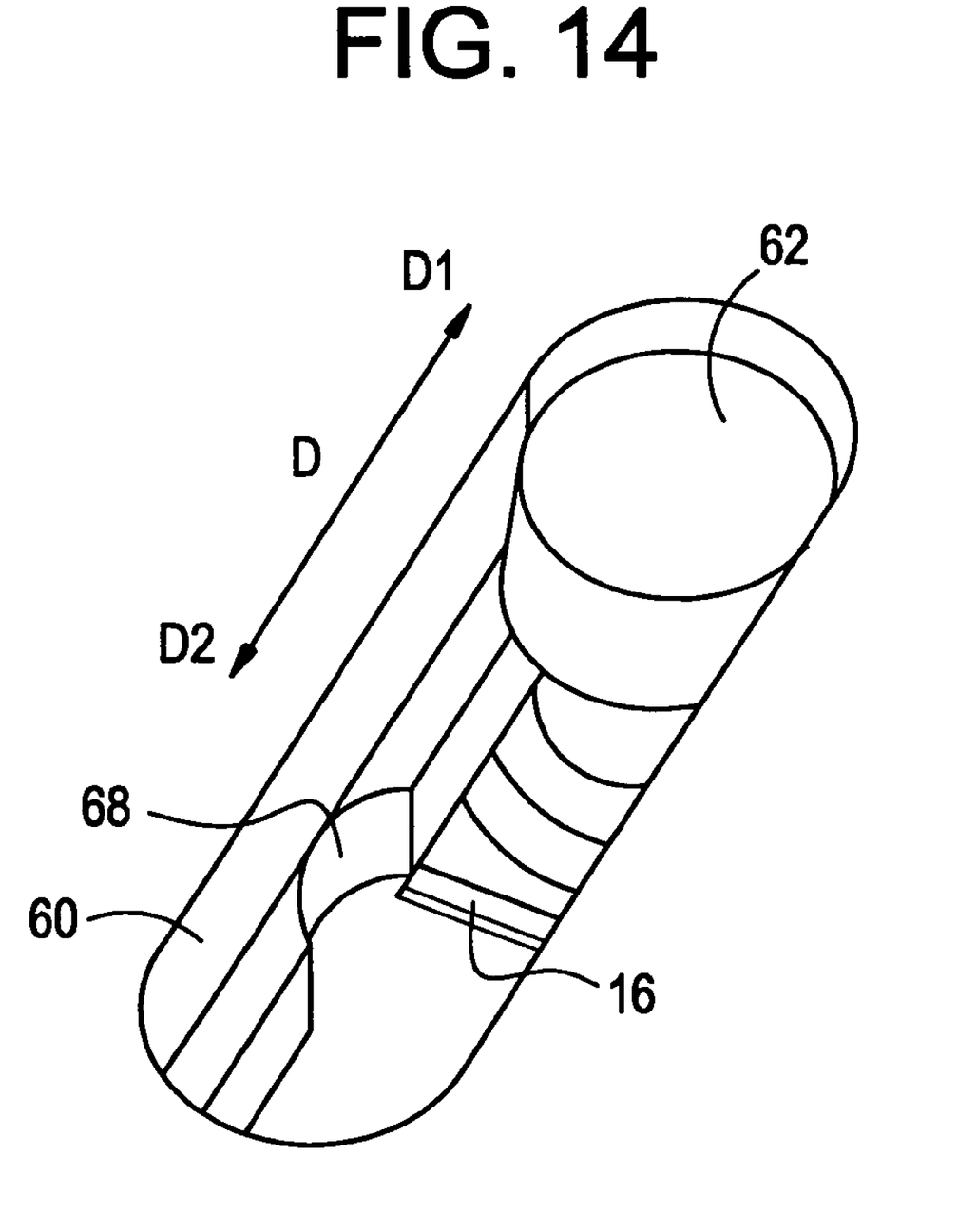
FIG. 14 is a three-dimensional top view of one embodiment of a key slot.

As further shown in FIG. 12, the bone plate 12 includes a key hole 60 and a slot 58. The biasing member 18 is positioned in the slot 58, and the biasing member 18 is retained in the bone plate 12 by the slot 58. As further shown in FIGS. 13 and 14, the first and second retainers 16 and 116 include keyed ends 62 and 162, respectively, that are positioned and held in the key hole 60. As shown in FIGS. 12 and 14, the bone plate 12 also includes an insertion opening 68. The keyed ends 62 and 162 are placed through the insertion opening 68 such that the first and second retainers 16 and 116 are retained in the bone plate 12. The movement of the first and second retainer 16 and 116 in the bone plate 12 is movement within the key hole 60. The biasing member 18 is positioned such that movement of the first and second retainers 16 and 116 in the key hole 60 will elastically deform the biasing member 18. Thus, when moved, the first and second retainers 16 and 116 will be caused to move back to positions A and A', respectively, by a force from the elastically deformed biasing member 18.

As further shown in relation to FIGS. 1-4 and 10-11, the aperture 14 can be tapered from the top surface 70 to the bottom surface 72. It should also be appreciated the aperture 14 of the bone plate 12 can have countersink dimensioning that is complementary to the head 22 of the bone anchor 20 such that a tapered portion 64 (FIG. 13) of the head 22 or the entire head 22 can sit below the top surface 70 (FIG. 3) of the bone plate 12. Further, it should be appreciated that any descriptions of the aperture 14 in the bone plate 12 can extend to all apertures 14 in the bone plate 12 if the bone plate has more than one aperture 14.

The foregoing discussion of the invention has been presented for purposes of illustration and description. Further, the description is not intended to limit the invention to the form disclosed herein. Consequently, variations and modifications commensurate with the above teachings and with the skill and knowledge of the relevant art are within the scope of the present invention. The embodiment described herein above is further intended to explain the best mode presently known of practicing the invention and to enable others skilled in the art to utilize the invention as such, or in other embodiments, and with the various modifications required by their particular application or uses of the invention. It is intended that the appended claims be construed to include alternative embodiments to the extent permitted by the prior art.

What is claimed is:

1. A medical implant using a bone anchor for attachment of the medical implant to a boney element, the medical implant comprising:
   a bone plate having an aperture therethrough, said aperture adapted to receive at least a portion of said bone anchor, wherein said bone plate includes a seat extending in a first direction transversely to and away from said aperture into said bone plate;
   a retention mechanism coupled to said bone plate, said retention mechanism comprising a retainer and a biasing member adapted to be operatively engaged with at least said retainer; said retainer moveable to and from at least a first position and a second position, said first position allowing said bone plate to receive said bone anchor in said aperture, said second position allowing said retention mechanism to retain said bone anchor in said bone plate, wherein said retainer moves linearly in said seat in said first direction and opposite said first direction between said first and second positions with said biasing member normally biasing said retainer to said second position,
   wherein insertion of said bone anchor in said aperture causes said retainer to linearly move in said first direction from said second position to said first position and elastically deform said biasing member, and wherein said biasing member causes said retainer to linearly move opposite said first direction toward said aperture to said second position to retain said bone anchor in said bone plate, wherein:
   said bone plate further comprises first and second channels extending along opposite sides of said seat and said retainer includes tabs extending from opposite sides thereof, said tabs sliding along respective ones of said first and second channels when moving between said first and second positions with said first and second channels capturing said retainer in said bone plate; and
   said seat includes a stop extending therein adjacent to said aperture, said seat further defining grooves on opposite sides of said stop, and said retainer includes contacting portions extending from a bottom surface of said retainer, said contacting portions being configured to move through said grooves as said retainer moves between said first and second positions.

2. The medical implant of claim 1, wherein said retainer includes an opening extending therethrough that is positioned over said seat and said biasing member is positionable into said seat through said opening with said biasing member located in said seat in contact with said stop and said contacting portions compress said biasing member against said stop when moving from said second position to said first position.

3. The medical implant of claim 1 wherein said biasing member comprises a spring.

4. The medical implant of claim 1 wherein said biasing member comprises a flexible ring.

5. The medical implant of claim 4 wherein said flexible ring comprises a shape memory alloy.

6. The medical implant of claim 1 wherein said bone anchor further comprises a head having a tapered portion circumferentially located about said head, and wherein insertion of said bone anchor in said aperture causes said tapered portion to contact said retainer and causing said retainer to move to said first position.

7. The medical implant of claim 6 wherein said retainer comprises a first end and a second end positioned opposite from said first end, said first end adapted to engage said biasing member and said second end comprising a contoured edge for contacting said tapered portion of said head of said bone anchor.

8. The medical implant of claim 6 wherein said bone anchor further comprises an engagement portion positioned on a top of said head portion, said engagement portion contacting said retainer whereby retaining said bone anchor in said bone plate.

9. The medical implant of claim 8 wherein when said retainer is in said second position a portion of said head of said bone anchor is positioned below a portion of said retainer.

10. The medical implant of claim 1 wherein said bone plate further comprises a plurality of apertures and a plurality of retention mechanisms. wherein a one of said plurality of retention mechanisms corresponds to a one of said plurality of apertures.

11. The medical implant of claim 1 wherein said bone plate further comprises a first aperture and a second aperture and said bone anchor comprises a first bone anchor and a second bone anchor, said retainer moveable to and from at least said first position, said second position and a third position, said first position allowing said bone plate to receive said first bone anchor in said first aperture, said third position allowing said bone plate to receive said second bone anchor in said second aperture, and said second position allowing said retention mechanism to retain said first bone anchor an said first aperture and said second bone anchor in said second aperture of said bone plate,
   wherein insertion of said first bone anchor in said first aperture causes said retainer to move to said first position and elastically deform said biasing member, wherein insertion of said second bone anchor in said second aperture causes said retainer to move to said third position and elastically deform said biasing member, and wherein said biasing member causes said retainer to move to said second position to retain said first and second bone anchors in said bone plate.

12. A medical implant using a first: and second bone anchor for attachment of the medical implant to a boney element, the medical implant comprising:
   a bone plate having a first aperture and a second aperture, said first and second apertures located through said bone plate, said first aperture adapted to receive at least a portion of said first bone anchor, said second aperture adapted to receive at least a portion of said second bone anchor, said bone plate further including a seat extending in a first direction from said first aperture to said second aperture; and
   a retention mechanism coupled to said bone plate, said retention mechanism comprising a retainer and a biasing member adapted to be operatively engaged with at least said retainer, said retainer moveable to and from at least a first position, a second position and a third position, said first position allowing said bone plate to receive said first bone anchor in said first aperture, said second position allowing said bone plate to receive said second bone anchor in said second aperture, said third position allowing said retention mechanism to retain said first and second bone anchors in said bone plate, wherein said retainer moves linearly in said seat in said first direction from said third position to said first position and said retainer moves linearly in said seat opposite said first direction from said third position to said second position and said biasing member normally biases said retainer to said third position, wherein insertion of said first bone anchor in said first aperture causes said retainer to linearly move in said first direction from said third position to said first position and elastically deform said biasing member, wherein insertion of said second bone anchor in said second aperture causes said retainer to linearly move opposite said first direction from said third position to said second position and elastically deform said biasing member, and wherein said biasing member causes said retainer to linearly move from either of said first and second positions to said third position to retain said first and second bone anchors in said bone plate, wherein:

wherein said bone plate further comprises first and second channels extending along opposite sides of said seat and said retainer includes tabs extending from opposite sides thereof, said tabs sliding along respective ones of said first and second channels when moving from said third position to said first and second positions with said first and second channels capturing said retainer in said bone plate; and said seat includes a first stop extending therein adjacent to said first aperture, a second stop extending therein adjacent to said second aperture, said seat further defining grooves on opposite sides of each of said first and second stops, and said retainer includes contacting portions extending from a bottom surface of said retainer, said contacting portions being configured to move through said grooves as said retainer moves from said third position to said first and second positions.

13. The medical implant of claim 12 wherein said retainer includes an opening extending therethrough that is positioned over said seat and said biasing member is positionable into said seat through said opening with said biasing member located in said seat in contact with said first and second stops and said contacting portions of said retainer compress said biasing member against said second stop when moving from said third position to said first position and said contacting portions of said retainer compress said biasing member against said first stop when moving from said third position to said second position.

14. The medical implant of claim 12 wherein said biasing member comprises a spring.

15. The medical implant of claim 12 wherein said biasing member comprises a flexible ring.

16. The medical implant of claim 15 wherein said flexible ring comprises a shape memory alloy.

* * * * *